United States Patent [19]

Petrov et al.

[11] Patent Number: 5,786,334
[45] Date of Patent: Jul. 28, 1998

[54] HEXAPEPTIDE HAVING IMMUNOSTIMULATORY ACTIVITY

[75] Inventors: Rem V. Petrov; Agusta A. Mikhatlova; Stanklav Jn. Shanurin; Ludmila A. Zakharova; Larissa A. Fonina; Elena A. Kirilina; Sergey A. Gur'yanov, all of Moscow, Russian Federation

[73] Assignee: Technology Resources International, Inc., Arlington, Va.

[21] Appl. No.: 143,815

[22] Filed: Oct. 27, 1993

Related U.S. Application Data

[63] Continuation-in-part of Ser. No. 928,817, Aug. 14, 1992, abandoned.

[51] Int. Cl.⁶ .............................. C07K 7/06; A61K 38/08

[52] U.S. Cl. ..................... 514/17; 424/185.1; 530/329
[58] Field of Search ........................ 514/17; 530/329; 424/185.1

[56] References Cited

PUBLICATIONS

Dokl. Akad. Nauk SSSR(3), 755–757 (1991).
Fonina et al., Chem Abstract CA 116(1); 4237u (1991).
Dokl. Akad. Nauk SSSR 319(3), pp. 755–757.

*Primary Examiner*—Howard E. Schain
*Attorney, Agent, or Firm*—Armstrong. Westerman. Hattori. McLeland & Naughton

[57] ABSTRACT

The hexapeptide Phe—Leu—Gly—Phe—Pro—Thr, which is derived from a myelopeptide, exhibits immunostimulatory activity when administered to a mammal.

6 Claims, 2 Drawing Sheets

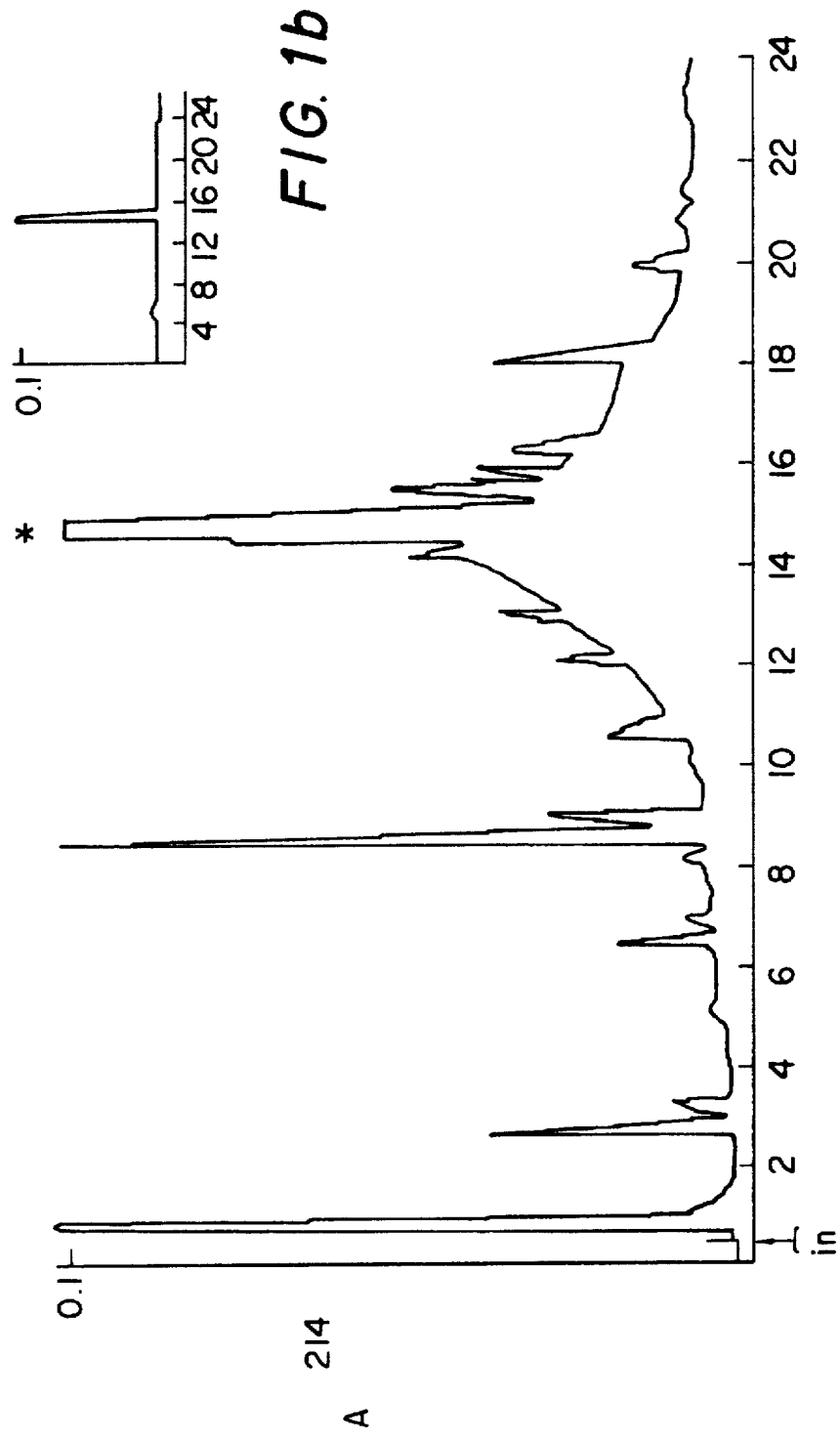

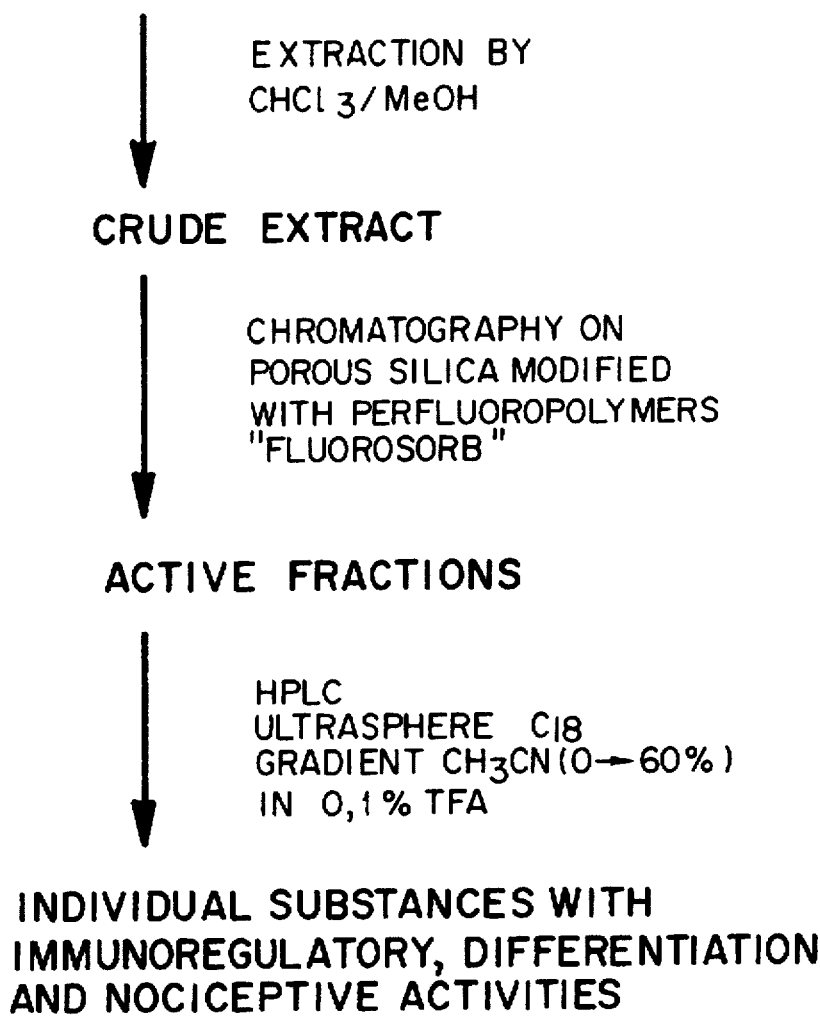

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
  ( A ) LENGTH: 4 amino acids
  ( B ) TYPE: amino acid
  ( D ) TOPOLOGY: linear ( i i ) MOLECULE TYPE: peptide ( v i ) ORIGINAL SOURCE:
  ( A ) ORGANISM: Sus scrofa
  ( G ) CELL TYPE: blood ( x i ) SEQUENCE DESCRIPTION: SEQ ID NO:1:

Tyr Pro Trp Thr
 1

( 2 ) INFORMATION FOR SEQ ID NO:2:

( i ) SEQUENCE CHARACTERISTICS:
  ( A ) LENGTH: 5 amino acids
  ( B ) TYPE: amino acid
  ( D ) TOPOLOGY: linear ( i i ) MOLECULE TYPE: peptide ( v i ) ORIGINAL SOURCE:
  ( A ) ORGANISM: Homo sapiens
  ( G ) CELL TYPE: blood ( x i ) SEQUENCE DESCRIPTION: SEQ ID NO:2:

Thr Ser Lys Tyr Arg
 1         5

( 2 ) INFORMATION FOR SEQ ID NO:3:

( i ) SEQUENCE CHARACTERISTICS:
  ( A ) LENGTH: 6 amino acids
  ( B ) TYPE: amino acid
  ( D ) TOPOLOGY: linear ( i i ) MOLECULE TYPE: peptide ( v i ) ORIGINAL SOURCE:
  ( A ) ORGANISM: Sus scrofa (F) TISSUE TYPE: bone marrow (x i) SEQUENCE DESCRIPTION: SEQ ID NO:3:

```
Phe  Leu  Gly  Phe  Pro  Thr
1                  5
```

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (vi) ORIGINAL SOURCE:
        (A) ORGANISM: Sus scrofa
        (F) TISSUE TYPE: bone marrow (x i) SEQUENCE DESCRIPTION: SEQ ID NO:4:

```
Leu  Val  Val  Tyr  Pro  Trp
1                  5
```

HEXAPEPTIDE HAVING IMMUNOSTIMULATORY ACTIVITY

This application is a continuation-in-part of U.S. Ser. No. 07/928,817 filed Aug. 14, 1992, which application is hereby incorporated by reference.

BACKGROUND OF THE INVENTION

Bone marrow cells secrete myelopeptides ("MP"). Myelopeptides are humoral factors that stimulate the immune system and cell differentiation. A mixture of unidentified MPs has been used in the Soviet Union, in both human and veterinary applications for a variety of effects.

Many MPs are known to have an opiate-like analgetic effect. These substances influence pain sensitivity in an oppositely directed pattern depending on the MP dose. The hyperalgesic effect of MP correlates with the immune response stimulation. (Zakharova et al. *Participation of Opioids in the Immunostimulatory Activity of Myelopeptides*, 1, Biomed. Sci., 139–143 (1990)). The opiate receptors mediate some hypoalgesic effects of MP.

MPs have been reported, both in vitro and in vivo to stimulate an immune response. For example, the literature reports that both adding MPs to a mature antibody forming cell culture (AFC) or injecting MPs into animals at the peak of their immune response to an antigen, resulted in a 2–5 fold increase in the level of antibody production. Other stimulants, such as: thymus peptides, mitogens, and Freund's adjuvant, do not show a stimulation effect under similar experimental conditions. (Petrov et al., *Regulatory Bone Marrow Peptides and Immunocorrection*, 2, EOS, 88–93 (1987)).

Additionally, the authors suggest that MPs can correct some defects of immunity. Specifically, the authors report that injecting MPs into MRL/lpr mice with a congenital autoimmune disorder normalizes both their antibody response to sheep red blood cells (SRBC) and their level of circulating immune complexes in blood. These authors further report a decline in the level of B-cell polyclonal activation in the injected mice. The authors also report that correcting these immune disorders with MP injections was accompanied by 2-fold increase in longevity (Mikhailova et al., *Myelopeptides Effect on Longevity and Immunological Parameters in Mice with Congenital Immunodeficiency*, 27, ANN. INS. SUPER. SANITA, 56–60 (1991)). The MPs were also reported to normalize in vitro defective Ig synthesis in pokeweed mitogen—(PWM) stimulated human peripheral blood lymphocytes. The PWM—stimulated lymphocytes were obtained from both healthy PWM nonresponder donors and patients with hypoglobulinemia (Jahn et al., *A Myelopeptide from Unstimulated Bone Marrow Cells with Immunoregulatory Activity*, 10, INT. J. IMMONOPHARMAC., 23–28 (1988)).

Proteolytic hydrolysis of hemoglobin produces fragments that possess opioid activity. Specifically, hemoglobin fragments hemorphin-4 (Tyr—Pro—Trp—Thr), the β-chain sequence of porcine (34–37) and human (32–35) hemoglobin which have opioid activity (Brantl et al., *Novel Opioides Derived From Hemoglobin: Hemorphins*, EUR. J. PRM., 309–10 (1986)). The hemoglobin α-chain contains the neokyotorphin peptide Thr—Ser—Lys—Tyr—Arg (137–141 amino acid residues) which peptide has hypoalgetic activity (Zhu et al., *Neo-Kyotorphin, An Analgesic Peptide Isolated From Human Lung Carcinoma*, FEBS LETTERS, 253–57 (1986)). There are no data on immunoregulatory activity of hemoglobin fragments.

SUMMARY OF THE INVENTION

We identified and determined the primary structure of a peptide that affects nociceptive sensitivity and stimulated antibody production. The peptide has been purified so that it comprises at least about 10% of the resulting composition, as well as at least about 25, 50 and 90% of the resulting composition.

BRIEF DESCRIPTION OF THE FIGURE

FIG. 1a shows the elution profile on an Ultrasphere ODS C18 HPLC column using an acetonitrile gradient in trifluoroacetic acid solvent system of a Phtorosorb column fraction containing pain sensitivity activity;

FIG. 1b shows the elution profile, under the same conditions, of a re-chromatography of the active fraction from the HPLC column;

FIG. 2 shows a schematic representation of the separation methods used herein;

DETAILED DESCRIPTION OF THE INVENTION

Separation Method

We isolated peptides from 1000 L of serum-free water soluble portion of the supernatant of an 18 hour cultures of porcine bone marrow cells. We lyophilized the supernatant and extracted hydrophobic material with a methanol-chloroform mixture (1 parts methanol to 1 part chloroform).

We then separated the extract into fractions on a macropore glass modified by perfluoropolymer (Phtorosorb) column. The material of interest was eluted from the Phtorosorb column using an acetonitrile gradient (0 to 50%) over 150 min. at a rate of 2 ml/min. Using this method we obtained 23 chromatographic fractions.

We tested the Phtorosorb column fractions using the Ankier method (Ankier et al., *New Hot Plate Tests To Quantify Antinociceptive and Narcotic Antagonists Activities*, EUR. J. PHARM., 1–4, 1974) (described below), which we hereby incorporate by reference, to determine which fractions contained material that influenced pain sensitivity.

We tested the Immunostimulatory activity of the fractions by their ability to increase the antibody production in lymph node cells. We obtained the lymph node cells from mice at the peak of the secondary immune response to SRBC. (Petrov et al. *Cell interaction in the immune response: effect of humoral factor released from bone marrow cells on the quantity of mature antibody producers in culture of immune lymph node cells*, 17, CELL IMMUNOL., 342–358 (1975)) which we hereby incorporate by reference.

The most promising fractions were chosen for the further separation and purification using reverse phase high performance liquid chromatography ("RP HPLC"). Specifically, seven fractions which had an immunostimulating effect and three fractions that effected the pain sensitivity were further purified by RP HPLC. This further separation isolated some individual bioactive molecules.

For example, we obtained a non-peptide substance with hypoalgesic effect from fraction 4. This substance has a molecular weight of about 607 daltons.

We also identified a mixture of two peptides that modulate pain sensitivity inducing hypoalgesia in high pain sensitivity threshold and hyperalgesia in low pain sensitivity threshold in fraction 11. We determined the primary structure of these two peptides.

Thereafter, we found several substances having immunostimulating activity. But, we have not determined the primary structure of these peptides as N-terminus of these peptides is blocked.

We further separated a fraction the material that eluted about 82 minutes after the eluate started leaving the Phtorosorb column. This fraction contained material that influenced pain sensitivity. We further separated this material by HPLC using a C18 (Ultrasphere ODS, 0.5×15 cm) reversed phase column. We eluted material from the C18 column using a linear 5 to 48% acetonitrile gradient over 24 minutes in a 0.1% trifluoroacetic acid solvent system at an elution rate of 1 ml/min. (FIG. 1a). Using this method, we obtained HPLC fractions.

We tested the HPLC column fractions for pain sensitivity activity, again by the Ankier method. The most promising fraction for pain sensitivity activity corresponded to peak 2 in the chromatogram of FIG. 1a whereas the fraction most promising in antibody stimulating activity corresponded to peak 1 on that chromatogram.

We found that the HPLC column fraction having the greatest pain sensitivity activity contained two peptides. We sequenced these isolated peptides on a liquid phase sequencer Applied Biosystem 477A/120A (USA). High performance capillary electrophoresis was performed on an Applied Biosystem 270A instrument (USA).

The amino acid sequencing of the isolated fraction revealed two hydrophobic hexapeptides of the following structure: Phe—Leu—Gly—Phe—Pro—Thr (40%) and Leu—Val—Val—Tyr—Pro—Trp (60%). Through a data bank search for homologous structures in known protein sequences (PIR 1990), we found that peptide (1) is within the N-terminal fragment of the β-chain (33–38), and peptide (2) is within the N-terminal fragment of the β-chain (31–36) of porcine hemoglobin. The sequences are highly conservative fragments of vertebrate hemoglobins.

In view of the similar physicochemical properties of these two peptides, we could not separate them from each other by RP HPLC under various conditions or by high performance capillary electrophoresis. Therefore, we tested the activity of a mixture of two peptides.

Our data on the functional activities of peptide fragments is reported in Table 1. The peptide mixture manifests modulatory action depending on the level of the pain threshold for control animals. At a high pain sensitivity threshold (>25 sec), the peptides induced a decrease in the latent period of the pain response by 27–33% of the control level (Table 1, 2 and 3b). A hypoalgetic effect (20% increase) of peptides is observed at a low sensitivity threshold (>20 sec) (Table 1, 1). At a mean level of the sensitivity threshold the peptide injection does not change it (Table 1, 3a).

Thee peptide mixture also prevented the development of post-pain hypoalgesia induced by pain stimulus. After the primary determination of the pain sensitivity threshold (two hours later) the pain sensitivity threshold increased by 36% in control animals, whereas the latent period of the pain reaction did not change in the experimental animals (Table 1, 3a, b).

TABLE 1

Effect of hexapeptides isolated from cultures of bone marrow cells on pain sensitivity of hybrid mice, (CBAxC57B1)F1.

| Group of mice with different pain threshold | Latency time of nociceptive reaction (sec) M + m* | | % of control | P** |
|---|---|---|---|---|
| | control | experiment | | |
| 1 low | 19.1 ± 1.6 | 23.1 ± 2 | 121 | <0.1 |
| 2 high | 29.2 ± 2.5 | 19.6 ± 1.7 | 67 | <0.05 |
| 3*** normal a | 22.0 ± 0.9 | 22.6 ± 1.3 | 103 | >0.05 |
| 3 normal b | 30.1 ± 2.7 | 22.0 ± 1.7 | 73 | <0.05 |

*Standard error of mean.
**One-tailed (Student's) T test.
***Stress-induced hypoalgesia. The measurement of the pain sensitivity threshold was performed in 2 h after pain thermal stimulation.

Ankier Method

In using the Ankier Method to estimate pain sensitivity, we placed mice (CBA×C57B1)F1 on a (50° C.) hot plate. Each group of experimental animals (mice) consisted of 5 mice. Solutions of the tested peptide (100 pmol) in 0.2 ml of physiological solution, were injected once intraperitoneally into each subject in a test group. The mice in the control groups received 0.2 ml of physiological solution. The pain sensitivity threshold was detected by the latent time of the nociceptive reaction of animals in 30 min. after the administration of the studied substances. Each animal was tested once.

Special experiments were carried out to study the influence of the peptides on stress induced hypoalgesia developed in 2 h after the primary detection of the pain sensitivity threshold, i.e., in 2.5 h after the injection of fractions or physiological solution. In the mice with medium level of pain sensitivity threshold (22.0±0.9) there was no significant difference between control and experimental groups (3 normal a). Determination of the pain sensitivity threshold in the same mice two hours later (again using the Ankier method) showed increase of this parameter by 36% in control animals (hypoalgesia) but not in experimental group (3 normal b). This data suggests that these hexapeptides prevented the development of stress-induced hypoalgesia.

Subsequently, we synthesized the two hexapeptides we identified and tested the effect of the individual hexapeptides on pain sensitivity, again using the Ankier Method. The result of this work with the synthesized hexapeptides is summarized in Table 2.

TABLE 2

Effect of hexapeptides (α-and β-chains) on pain sensitivity of hybrid mice, (CBA x C57BL)F1

| Dose of peptides g (mice) | Latency time of nociceptive reaction (Sec) M ± m | |
|---|---|---|
| | α-chain | β-chain |
| control | 18.2 ± 1.6 | 21.0 ± 2.1 |
| $10^{-9}$ | — | 20.2 ± 0.8 |
| $10^{-8}$ | 11.6 ± 1.1** | 18.4 ± 2.4 |
| $10^{-7}$ | 14.0 ± 1.8* | 21.5 ± 1.4 |
| $10^{-6}$ | 15.4 ± 3.8 | 18.9 ± 2.6 |
| $10^{-5}$ | 14.5 ± 2.2 | 17.4 ± 1.5 |
| $10^{-4}$ | 19.2 ± 1.4 | |

*Significantly different from control, p < 0.05.
**Significantly different from control, p < 0.01.

As the above data demonstrates, only the α-chain was active.

We also tested the α- and β-chains for immunostimulatory activity. We assayed immunostimulatory activity by the ability of the tested peptides to stimulate antibody production.

We immunized 30 (CBA×C57B1)F1 mice with 0.1 ml of SRBC (5%) into each of the four footpads (i.e., a total injection volume of 0.4 ml). On the 4th day after a secondary immunization, we sacrificed the mice and removed their regional lymph nodes. We then prepared a suspension from lymph node cell ($2 \times 10^6$ cells/ml) and incubated, in test wells, this suspension in the presence of (i) the a-chain, (ii) the β-chain, (iii) and a control with neither peptide. Each well contained $2 \times 10^5$ cells in 0.2 ml.

After a 20-hour incubation, we indirectly determined the number of AFCs by Jerne's method (Dresser et al., 288 NATURE, 854–861 (1965)). We then calculated the stimulation coefficient, the ratio of AFC number for a well to the control well AFC number. The α-chain, but not the β-chain, stimulated 1.8 fold increase in antibody production at the doses between $10^{-9}$ and $10^{-13}$ g/ml.

We also studied α-chain's ability to restore antibody formation in irradiated mice. We irradiated 30 (CBA× C57B1)F1 mice with γ-rays at a sublethal dose (2 GU). Two weeks after irradiation, we immunized these mice with SRBCs. Five days after the SRBC injection, we sacrificed the mice and determined the number of AFCs in their spleens.

Before sacrificing the mice, we injected them with the α-chain in one of three ways: (i) a single injection simultaneously with SRBC; (ii) a single injection at the peak of immune response; or (iii) daily injections during 4 days of immune response. We also gave a control group of irradiated mice a single saline injection. α-Chain induced an AFC elevation in each case. However the maximum AFC response was observed with daily injections. The enhancement of antibody production was up to 67.5–81.2% compared with 0.30% in control irradiated group

What we claim is:

1. A hexapeptide of the formula Phe—Leu—Gly—Phe—Pro—Thr.

2. A humoral immunostimulatory composition comprising a hexapeptide of the formula Phe—Leu—Gly—Phe—Pro—Thr and a pharmaceutically acceptable carrier.

3. A method of stimulating the humoral immune response to an antigen in a mammal which comprises administering to the mammal a humoral immunostimulatory effective amount of a hexapeptide of the formula Phe—Leu—Gly—Phe—Pro—Thr.

4. In a method for enhancing antigen-induced antibody formation in a mammal, the improvement which comprises administering to the mammal a humoral immunostimulatory effective amount of a hexapeptide of the formula Phe—Leu—Gly—Phe—Pro—Thr.

5. A method of stimulating the humoral immune response to an antigen in a mammal in need of having said immune response stimulated, which comprises administering to the mammal a humoral immunostimulatory effective amount of a hexapeptide of the formula Phe—Leu—Gly—Phe—Pro—Thr.

6. In a method for enhancing antigen-induced antibody formation in a mammal, in need of having said antibody formation enhanced, the improvement which comprises administering to the mammal a humoral immunostimulatory effective amount of a hexapeptide of the formula Phe—Leu—Gly—Phe—Pro—Thr.

* * * * *